United States Patent
Bak

(10) Patent No.: US 8,779,386 B2
(45) Date of Patent: Jul. 15, 2014

(54) ASSEMBLY AND METHOD FOR DISINFECTING LUMENS OF DEVICES

(75) Inventor: Jimmy Bak, Greve (DK)

(73) Assignee: U-VIVO ApS, Roskilde (DK)

( * ) Notice: Subject to any disclaimer, the term of this patent is extended or adjusted under 35 U.S.C. 154(b) by 0 days.

(21) Appl. No.: 13/582,591

(22) PCT Filed: Mar. 3, 2011

(86) PCT No.: PCT/EP2011/053180
§ 371 (c)(1),
(2), (4) Date: Sep. 4, 2012

(87) PCT Pub. No.: WO2011/107540
PCT Pub. Date: Sep. 9, 2011

(65) Prior Publication Data
US 2012/0321509 A1    Dec. 20, 2012

Related U.S. Application Data

(60) Provisional application No. 61/309,987, filed on Mar. 3, 2010.

(30) Foreign Application Priority Data

Mar. 3, 2010    (EP) ..................... 10155297

(51) Int. Cl.
*G01N 23/00* (2006.01)
*A61N 5/00* (2006.01)
(52) U.S. Cl.
USPC .................. 250/455.11; 250/492.1
(58) Field of Classification Search
USPC .................. 422/1, 22, 24; 250/455.11, 492.1
See application file for complete search history.

(56) References Cited

U.S. PATENT DOCUMENTS

2007/0176117 A1*  8/2007  Redmond et al. ........ 250/455.11
2008/0051736 A1   2/2008  Rioux et al.
(Continued)

FOREIGN PATENT DOCUMENTS

EP    2161040 A1    3/2010
WO    02/102421 A1  12/2002
(Continued)

OTHER PUBLICATIONS

International Search Report and Written Opinion received for PCT Patent Application No. PCT/EP2011/053180, mailed on Apr. 13, 2011, 12 pages.

(Continued)

*Primary Examiner* — Monzer R Chorbaji
(74) *Attorney, Agent, or Firm* — Morrison & Foerster LLP

(57) ABSTRACT

The invention relates to an assembly for disinfecting/sterilizing surfaces and lumens of a device with a light source which emits disinfecting/sterilizing light. The assembly comprises a device (9) for transporting fluid having a lumen and a connector part (10), at least one light source (100) configured to emit light having disinfecting/sterilizing effect, and a separate unit (8); where the light source (100) comprises: a housing (1) comprising a light emitting unit (11) emitting light having disinfecting/sterilizing effect and a connector part (5). The separate unit (8) comprises: an optical window (4) being transparent for light emitted from the light emitting unit (11), a first coupling part and a second coupling part, where the first coupling part during use is attached to the connector part (5) of the light source (100), and the second coupling part during use is attached to the connector part (10) of the device, such that the device (9) are in complete extension of the light source (100) with no overlap, and the first coupling part is located at one side of the optical window (4) and the second coupling part is located on the other side of the optical window (4), when disinfection/sterilization of the device takes place.

17 Claims, 7 Drawing Sheets

(56) References Cited

U.S. PATENT DOCUMENTS

2008/0306454 A1  12/2008  Sikora
2009/0012459 A1   1/2009  Sobue et al.

FOREIGN PATENT DOCUMENTS

WO    2008/014437  A2    1/2008
WO    2010/023329  A1    3/2010

OTHER PUBLICATIONS

International Preliminary Report on Patentability received for PCT Patent Application No. PCT/EP2011/053180, mailed on Apr. 12, 2012, 8 pages.

* cited by examiner

ASSEMBLY AND METHOD FOR DISINFECTING LUMENS OF DEVICES

CROSS REFERENCE TO RELATED APPLICATIONS

This is a U.S. National Phase patent application of PCT/EP2011/053180, filed Mar. 3, 2011, which claims priority to the U.S. Provisional Patent Application No. 61/309,987, filed Mar. 3, 2010, and the European Patent Application No. 10155297.4, filed Mar. 3, 2010, each of which is hereby incorporated by reference in the present disclosure in its entirety.

THE TECHNICAL FIELD

The invention relates to an assembly for disinfecting/sterilizing surfaces and lumens of a device with a light source which emits disinfecting/sterilizing light. The assembly comprises a device having a lumen, a light source configured to emit disinfecting/sterilizing light into the lumen of the device and a separate unit. The light source comprises a light emitting unit, which emits disinfecting/sterilizing UV light, and the separate unit is placed between the device and the light source, and connected to the device and the light source through coupling parts. The separate unit comprises an optical window, through which the emitted light reaches the inlet portion of the device to be disinfected/sterilized.

Intravascular catheters are indispensable in modern-day medical practice, particularly in intensive care units (ICUs). Catheter-related bloodstream infections (CRBSI) resulting from bacterial colonisation of an intravascular catheter are a significant clinical problem, magnified in recent years by the increasing use of intravascular catheters in intensive care, chemotherapy and total parental nutrition. In particular, central venous catheter-related infections are a common cause of bacteraemia and sepsis.

There are three routes by which infection can occur:
Intraluminal
Extraluminal
Haematogenous Most in-dwelling e.g. vascular catheters are colonized by microorganisms. The colonizing micro-organisms are usually imbedded in a biofilm layer, they are metabolically active and viable, and they can already be present 24 h after insertion of the catheter.

Organisms causing bloodstream infections generally enter the bloodstream from the skin insertion site or through the connecting hub of the catheter which remains outside the skin but haematogenous seeding and contamination of infused fluids are possible causes as well.

When following the extraluminal route skin organisms migrate from the skin insertion site along the external surface of the catheter, colonizing the distal intravascular tip of the catheter and ultimately causing bloodstream infection. When following the intraluminal route, organisms may be introduced into the hub e.g. by the hands of medical personnel. The subsequent colonization of the internal surface of the catheter may also cause bloodstream infection. Many clinicians feel reluctant to remove the catheter, because most patients with cuffed tunnelled catheters have exhausted all other options for vascular access.

Health-care institutions purchase millions of intravascular catheters each year. The incidence of CRBSI varies considerably by type of catheter, frequency of catheter manipulation, and patient-related factors (e.g., underlying disease and acuity of illness). Peripheral venous catheters are the devices most frequently used for vascular access. Although the incidence of local or bloodstream infections associated with peripheral venous catheters is usually low, serious infectious complications produce considerable annual morbidity because of the frequency with which such catheters are used. However, the majority of serious catheter-related infections are associated with central venous catheters (CVCs), especially those that are placed in patients in ICUs.

In the ICU, central venous access might be needed for extended periods of time; patients can be colonized with hospital-acquired organisms; and the catheter can be manipulated multiple times per day for the administration of fluids, drugs, and blood products. Moreover, some catheters can be inserted in urgent situations, during which optimal attention to aseptic technique might not be feasible. Certain catheters (e.g., pulmonary artery catheters and peripheral arterial catheters) can be accessed multiple times per day for hemodynamic measurements or to obtain samples for laboratory analysis, augmenting the potential for contamination and subsequent clinical infection.

Specific examples of catheters causing problems are so-called peripherally inserted central catheters (PICCs), mid-line catheters, and peripheral catheters. A typical PICC, mid-line, or peripheral catheter contains a thin, flexible shaft, which contains one or more lumens and which terminates at the proximal end with a suitable fitting, such as a hub or other fitting. The primary difference between these three devices is the length of the tubing, with the peripheral catheter being the shortest and the PICC being the longest. The rationale for different lengths is driven by the type and duration of the therapy a patient is to receive.

Haemodialysis catheters are another important class of central venous access catheters. Haemodialysis catheters are commonly multi-lumen catheters in which one lumen is used to carry blood from the body to a dialysis machine, and another lumen returns blood to the body. Central venous access may be attained by puncture of various major blood vessels, including the internal jugular vein, subclavian vein, or femoral vein.

A catheter may further include various accessory components, for example, molded components, over-molded sub-assemblies, connecting fittings such as hubs, extension tubes, and so forth. Various catheter tips designs are known, including stepped tips, tapered tips, over-molded tips and split tips (for multilumen catheters), among others.

Respiratory circuits are another medical device where keeping a sterile environment is a challenge. Due to the inherent moisture and warmth, respiratory circuits provide superb conditions for microbiological growth or colonization. Once colonization has started, the microbiological growth can easily spread to the patient, either airborne or through moisture condensation running down into the patient's lungs, thus risking infections and complications, often resulting in pneumonia.

The problem of respiratory circuit colonization is especially prevalent within breathing tubes. For instance, studies have documented the health risks from colonization of biofilm in endotracheal tubes, which can be so extensive that the walls of the endotracheal tube become slimy and sticky.

Due to the close proximity to the patient's lungs, any microbiological growth in a breathing tube can easily spread to the patient's lungs. Condensed moisture can run down the breathing tube, over the biofilm and into the patient's lungs. Additionally, chunks of the biofilm can actually fall off the breathing tube and into the patient's lungs.

Other Optical Devices Used for Medical Diagnostics and Treatment

Medical devices such as endoscopes commonly employ light emitting components, such as light sources and light guides, for introducing light into the subject and various coupling designs are available, which readily allow the connection and disconnection of light emitting components to and from the device. For example, couplers and end fittings for optical cables, which allow for efficient coupling of light to and from the optical cables, are presently known in the medical arts including those available from Codman, Fuji, Pentax, Pilling, Storz, and Wolf, among others. Of course other designs, including other unthreaded and threaded designs, including Luer, press fit, and bayonet type couplings, among others, may be employed.

Disinfection with Ultraviolet-C (UVC) Light

It is known that microorganisms, such as viruses, bacteria, fungi, protozoa, algae, and so forth can be inactivated (i.e., either killed or prevented from reproducing, e.g., by molecular rearrangement of the microorganisms DNA) using light of various wavelengths, including ultraviolet light of various wavelengths such as ultraviolet-C (UVC) light having a wavelength of 100 to 280 nm, ultraviolet-B (UVB) light having a wavelength 280 to 320 nm, and ultra-violet-A (UVA) light having a wavelength of 320 to 400 nm. For example, UVC light has a very short wavelength and kills germs e.g. bacteria and viruses so well, that it is often used to disinfect/sterilize surfaces. UVB light has also been reported to kill microorganisms.

Several light sources emitting light with the same and/or different wavelengths having germicidal effects could be coupled together in a unit, wherein optics could capture and guide the emitted lights into the lumen of a device having disinfecting/sterilizing effect. Moreover, a light source could comprise several light emitting units, e.g. diodes with the same and/or different wavelengths having germicidal effects. By this a stronger disinfecting/sterilizing effect could be achieved.

PRIOR ART

US 2008/0051736 discloses a medical device in the form of an indwelling catheter provided with a light source configured such that light is transmitted from the light source into the catheter shaft or lumen for sterilization purposes. The intention is to sterilize the whole lumen of the catheter which is difficult as this necessitates that the light is guided from the light source through the length of the lumen e.g. this might necessitate that the material which the catheter has been constructed of can transmit light. Further the light source as e.g. seen in FIGS. 1A, 1B and 1C is integrated with the catheter into one assembly. This makes the assembly relatively expensive. Also it requires some dexterity and skills to correctly introduce or integrate the light source into the catheter and extract it i.e. this operation would be difficult for an elder patient. Furthermore, there is a risk of applying too much force during this process thereby breaking or compromising the light source. The configuration of the light source is not actually described in this document and also it is not possible to control whether the light from the light source is actually emitted with the expected effect.

US 2008/0051736 implies that each catheter has its own light source constructed to fit the specific lumen. In contrast, the present invention employs one configured light source which, in principal, can be coupled to different interfaces or coupling elements which are adapted to fit different devices e.g. catheters. This simplifies the method of sterilizing medical devices such as catheters and, as we will disclose, makes it simpler to couple the light source with the medical device.

The document US 2007/0176117 discloses a method and an apparatus for sterilizing access sites such as attachment points for various therapeutic and diagnostic medical devices. More particularly, the invention concerns a sterilization apparatus which includes a substantially UV-C transparent closure cap (16). The closure cap (16) is an UV-transparent cap which is attached to the access site; the apparatus for sterilizing the access site is provided with a cap receiving chamber (28) is formed within a capture member (32). Also mounted within the capture member (32) is a source of UV-C radiation for controllably emitting UV-C radiation in a direction towards cap receiving chamber (28). When the apparatus is to be used the closure cap (16) is first attached to the access site and then the assemblage of the UV-C transparent cap (16) and the access site is inserted through an opening (30) formed in the front wall of the housing and the cap (16) is guided into the receiving chamber (28). US 2007/0176117 does not provide a method for disinfecting/sterilizing the inner lumen parts of a device. The manual positioning of the closure cap (16) at the access site complicates the use of the apparatus.

WO 02102421 discloses methods and an apparatus for sterilizing/disinfecting using ultraviolet light or light emitting diodes (LEDs) using one or more several light sources and reflectors. WO 02102421 is primarily directed to a method for sterilizing/disinfecting interior surfaces of a catheter, through the wall of the catheter where the said wall is adapted and thinner allowing transmission of ultraviolet light through a lens and the said wall onto a stagnation zone. The stagnation area is an area where the diameter of the catheter changes and may therefore cause fluid to form eddies in the corners favoring colonization of bacteria. The disinfection apparatus disclosed by WO 02102421 has a clamshell configuration (FIG. 7A-7C) and comprises a disinfection chamber, wherein a portion of the catheter is placed, the clamshell is closed and the sterilization takes places. The opening (inlet portion) of the catheter can be placed in front of the light source, i.e. along the lumen of the catheter, thereby sterilizing the lumen and the interior surfaces of the catheter (FIG. 7A-7C). The catheter can also be placed so that the emitted sterilizing light is perpendicularly to the catheter walls sterilizing a part of the internal and external surfaces of the catheter (FIG. 8A-8C). In WO 02102421, the emitted sterilizing light is not guided and focused into the inlet portion of the medical device to be sterilized and the walls of the catheter to be sterilized has to be modified or constructed in such a way to allow UV transmission through the walls. Also, the clamshell configuration of the disinfection apparatus in WO 02102421 will only be suitable for some catheters which fit into the disinfection chamber.

The present invention is primarily directed to be used with medical devices comprising a shaft that contains one or more lumens (e.g., a tube, multilumen extrusion, etc.), which is introduced into a patient for either short or long term residency such as the medical devices described within the technical field.

The present invention is directed 1) to prevent intraluminal routed infections prophylactically and thereby hinder the formation of biofilm and 2) killing of biofilm when biofilm has been formed on the internal surfaces of the lumen of the medical device. The assembly can be used every time a catheter is used e.g. in dialysis or in various hospital equipment, such as internal lines in dialysis machines, hindering the occurrence of a biofilm layer and/or germs within the lumen of the catheter in a prophylactic manner.

The present invention is also directed to be used in non-medical devices with a lumen, were germs e.g. bacteria and biofilm can be deposited, e.g. in tubes in the food industry. Any article with a lumen e.g. a tube or pipe can be disinfected/sterilized either preventing or removing germs and/or biofilm deposition(s).

The object of the present invention is to provide a simply assembly where the light source can easily be coupled to any device, instrument, appliance or article which has a lumen, and stay coupled for as long as it is suitable. If the light source has to be in a use-position for more than a few minutes, the device therefore has to be able to stay in an on-condition, without having to be continuously held or influenced by any personnel or a patient if the device is e.g. medical device e.g. a catheter. Also, it is the object of the present invention, which the light source of the assembly should fit, or be easy to adapt by changing the thread/coupling part on the separate unit opposed to a new specific application, with all standard medical equipment which is in use at hospitals and clinics.

According to the present invention an external light source, emitting sterilizing/disinfecting light is placed outside and connected to the catheter or device lumen and connector. With an external light source it is achieved that:

- No parts of the catheter lumen are shadowed by the light source i.e. in principle all parts of the catheter and connector part can be swept by germicidal light from the light source.
- No time consuming cleaning and disinfection of the light source housing is necessary between usage of the source (i.e. between treatments and transfer between different lumens of the same catheter.
- It is possible to cool the light source and keep it at its optimal performance.
- No safety problems due to intra-luminal electrical wires and connectors.
- It is possible to perform maintenance check of the light source (measure power output and remove possible contamination on optical surfaces of the light source) before treatment is initiated in order to ensure the specified dose is delivered.

SUMMARY OF THE INVENTION

The present invention relates to an assembly comprising
a device for transporting fluid having a lumen and a connector part,
at least one light source (100) configured to emit light having disinfecting/sterilizing effect, and
a separate unit;
where the light source comprises:
a housing (1) comprising a light emitting unit emitting light having disinfecting/sterilizing effect and a connector part;
and where the separate unit comprises:
an optical window being transparent for light emitted from the light emitting unit,
a first coupling part and a second coupling part, where the first coupling part during use is attached to the connector part of the light source and the second coupling part during use is attached to the connector part of the device, such that the device are in complete extension of the light source with no overlap, and the first coupling part is located at one side of the optical window and the second coupling part is located on the other side of the optical window when disinfection/sterilization of the device takes place. That the device are in complete extension of the light source with no overlap means that the light source will emit light on the end parts of the device while the device will not touch the light source due to the optical window separating the device from the light source.

The optical window separates and forms a sterile barrier between the connector part of the device and the light source during use i.e when the light source is mounted to the device.

According to an embodiment, the connector part is formed in such a way, that no protruding parts create shadows in the connector part and its lumen. When protruding parts produce shadows micro organisms might be shaded and not subjected to the sterilizing light.

According to an embodiment, the connector part is a standard female Luer connector part with no protruding or UV non-transparent parts producing shadows in the lumen of the device.

According to an embodiment, the light source comprises a housing which comprises a light emitting unit emitting light having disinfecting/sterilizing effect or a photoactive effect, and an optical lens focusing the emitted disinfecting/sterilizing or photoactive light, and a second connector part.

According to an embodiment, the light source emits light having a wavelength between 250 nm and 700 nm.

According to an embodiment, the light source comprises an indicator adapted to show the expected life expectancy of the light emitting unit, where the light source is able to deliver a light having disinfecting/sterilizing effect.

According to an embodiment, the light emitting unit emits UVA or UVB or UVC or visible (VIS) light. According to this embodiment, the light emitting unit might be a UVA, a UVB, a UVC or a VIS LED diode, normally a UVC-LED diode.

According to an embodiment, a device can comprise a separate connector part combining to separate tubes e.g. having the same or different diameter (P1, P3), which separate connector part has a continuous transition (P2) having a constant or decreasing inner cross-sectional area. This construction prevents creation of shadows inside the combined tubes.

According to an embodiment, the assembly comprises more than one light source to be combined with one or more devices via a separate unit.

According to an embodiment, a light source is combined with a protective cap which together with a separate unit completely covers the light source. Such a protective cap or cover prevents contact between the outer surfaces of the light source and the patient and therefore the protective cap or cover removes the need for cleaning of the light source between uses. According to this embodiment, the protective cap (16) can be made of a thin flexible material such as a polymer and disposed off after use. Normally, the protective cap is intended for single use but it might be constructed in order to be used more than once and then sterilized in between uses.

According to an embodiment, the assembly comprises a power unit, e.g. comprising batteries and a remote control used to control time intervals for light doses. According to this embodiment, the power unit can be provided with a handle used to mount the power unit close to the patient without the patient actually carrying the power unit.

The assembly according to the invention can be used for disinfecting/sterilizing the inlet portion of the lumen and surfaces of a device such as a catheter. E.g. the assembly according to the invention can be used for disinfecting sterilizing the inlet portion of the endotracheal or tracheostomy tube in a subject.

According to a second aspect, the invention relates to a separate unit used to connect a device transporting fluid during use and a light source emitting light having disinfecting/sterilizing effect which separate unit comprises:

an optical window being transparent for light emitted from the light emitting unit, a first coupling part and a second coupling part, where the first coupling part during use is attached to the second connector part (5) of the light source (100), and the second coupling part during use is attached to the first connector part (10) of the device, such that the device (9) are in complete extension of the light source (100) with no overlap, and the first coupling part is located at one side of the optical window and the second coupling part is located on the other side of the optical window when disinfection/sterilization of the device takes place.

According to a third aspect, the invention relates to a method for disinfecting/sterilizing a device of an assembly according to the invention comprising the steps of:

a) Coupling a separate unit to a first part being either a device or a light source;
b) Coupling the separate unit to a second part being either a light source or a device;
c) Switching on the light source and disinfecting/sterilizing the device for a defined time period;
d) Disconnecting the light source from the separate unit;
e) Optionally disconnecting the separate unit from the device.

According to an embodiment of the method according to the invention, the method further comprises the step a) of:

a) Filling the lumen of a device to be disinfected or sterilized with a light guiding fluid before coupling the separate unit to the device. According to this embodiment, the material of the lumen of the device to be disinfected/sterilized, and/or the light guiding liquid(s) within the said lumen are chosen such that disinfection/sterilization of the outer surface of the lumen of the device is obtained.

According to one embodiment the necessary dosing time to obtain a disinfection/sterilization rate of 99.99% after preventive UVC light exposure is max 30 minutes. According to another embodiment the necessary dosing time to obtain a disinfection/sterilization rate of 99.99% after preventive UVC light exposure is less as possible, within 15 min, 10 min, 5 min, 3 min and within 1 minute(s).

DETAILED DESCRIPTION OF THE INVENTION

The present invention can be used in any technical field where devices with lumens are used for transporting fluid(s), i.e. liquid(s), gas(ses) or any other substance(s) were disinfection/sterilization of the lumen is required, either preventing or removing germs and/or biofilm depositions. The device(s) could also be part of any machine or instrument. The examples given below are merely to illustrate the use of the present invention, and should not be considered limiting in any way.

Medical Uses of the Present Invention

A medical device is a product used for medical purposes in patients e.g. used in in diagnosis, therapy or surgery i.e. in treatment. The medical device can be part of any article, instrument, appliance, medical equipment or any machine.

Normally, a device being part of the assembly according to the present invention fulfills the following conditions:

the device is in a state of use in contact both with an inside lumen of a patient, such as a vein or the trachea or another subcutaneous lumen, and with the skin surface of the patient, and a fluid in the form of either a gas or a liquid such as breathing air, blood, medication, a light guiding liquid or the like is flowing through the device or at least has access to or is positioned in the inner lumen of the device, and further the device is in the use position for a longer period defined as from 1 hour to several days.

Basically, the device is in the use position as long as treatment takes place and until it is removed due to complications such as device related infections, blood cloths and other obstructions ect.

Sterilization refers to any process that effectively kills or eliminates transmissible agents (such as fungi, bacteria, viruses, spore forms etc.) from any surface, from e.g. equipment, food products, medications, or biological culture medium. Sterilization is normally achieved through application of heat, chemicals, irradiation, or filtration or in any combination thereof.

Disinfection is defined as the cleaning of an article of some or all of the pathogenic organisms which may cause infection. Very few disinfectants and sanitizers can sterilize, i.e. completely kill all microorganisms.

The present invention can be employed both for sterilizing and for disinfecting lumens of devices.

The medical device will normally be a catheter, especially a catheter for indwelling use. In the description herein, the word catheter may refer to all types of catheters known in the art. The term catheter may include, for example, urinary, gastric, cardiovascular, and lung catheters, etc. In medicine a catheter is a tube that can be inserted into a body cavity or organ, duct or vessel through, for example, a body orifice or through a surgical procedure, and may be used for venting, feeding, injection of fluids (e.g. diagnostic agents and/or medicine), access for surgical instruments and/or drainage of air and/or liquids to and/or from the internal cavity or organ. In most uses a catheter is a thin, flexible tube i.e. a "soft" catheter; in some uses, it is a larger, solid tube i.e. a "hard" catheter. Furthermore, the term catheter may include catheters that are coated with chemo-prophylactic, biocide, antimicrobial and anti-infective drugs etc.

The present invention can be used on a medical device, e.g. a catheter, that is introduced/inserted into the body, e.g. in a vein, into an organ, or any intracavity catheter in any subject/mammal e.g. a human patient. The catheter could also be part of a device which is carried by, or has become part of the mammal e.g. an infusion device, an implant e.g. a pacemaker in human patient. The patient does need to be hospitalized or be bed-bound to utilize the present invention. The disinfecting/sterilizing light source of the present invention is versatile and mobile, such that a patient can move around, be at home while e.g. an indwelling catheter is being disinfected/sterilized on the patient.

The present invention can be used for/in any medical equipment, which has lumens were disinfection/sterilization is required, e.g. lumens/tubes or catheters in life supports systems, anesthesia ventilators, anesthesia units, fetal monitors, incubators, external pacemakers and heart lung machines.

Because of the need to prevent nosocomial bacterial or viral infections and mechanical accidents, and for economic reasons, inexpensive medical products, such as syringes, hypodermic needles and installations, in most cases are classified as disposable materiel and are used only once and then discarded as infective waste. However, fiberscopes such as gastrocameras and other types of endoscopes, including peritoneoscopes, thoracoscopes and arthoroscopes, and other expensive medical products, like catheters and similar intubation equipment, must in principle be employed repetitively. And due to the necessity to prevent infection, each time these medical devices are used they must be thoroughly cleaned by hand, or in an automatic washer, and must thereafter be dried, deodorized and sterilized.

This type of medical equipment epitomized by a fiberscope having a hollow portion, lumen or a narrow duct (a channel) that serves as a flow path for mucus or fluids or as an insertion path for forceps, for example, is a device that is extremely difficult to thoroughly clean and disinfect/sterilize.

The present invention also relates to a (prophylactic) method for keeping medical equipment cleaned and sterilized, or cleaning and sterilizing medical equipment, e.g. fiberscopes, such as gastrocameras and other types of endoscopes, including peritoneoscopes, thoracoscopes and arthoroscopes having hollow/duct/lumen portions, after use and medical supplies, such as catheters and tubes, that have long ducts or hollow portions, and that tend to be repetitively employed by being introduced into human bodies.

The present invention can also be used and/or adopted to sterilize endotracheal and tracheostomy tubes. Endotracheal and tracheostomy tubes are used to provide an airway in patients, who do not have an adequate airway due to medical conditions. An endotracheal tube (ET tube) is inserted through the mouth and larynx and into the trachea. Tracheostomy tubes are inserted through an incision just above the sternal notch. The present light source can be coupled to the upper end of the endotracheal or tracheostomy tube, which protrudes from the mouth or the trachea of a patient, disinfecting/sterilizing the inlet portion of the tube and the incoming/infused fluid. In human beings, mucociliary action regulates the flow of mucus across the layers of epithelial cells within air passages. This placement of the light source will still leave room for the passage of air through the endotracheal tube in an annular passage around the catheter. A fitting may be attached to the upper end of the catheter equipped with various ports so that the catheter may alternatively be connected to a vacuum source to provide suction, an irrigation port for lavage, for passage of an endoscope, etc.

Alternatively, the inner surfaces of the endotracheal tube and the catheter may be coated with a photocatalytic material with antimicrobial properties when exposed to ultraviolet light. Such materials may include titanium oxide, silicon oxide, zinc oxide, zirconium oxide, cadmium sulfate, metal oxides or combinations thereof. A light source, such as a light emitting diode (LED), which may be a UV LED, is attached to an upper portion of the endotracheal tube. Light emitted by the light source can also be carried by a fiberoptic bundle. The fibers pass through the endotracheal tube and illuminate the photocatalytic material.

Non-Medical Uses of the Present Invention

As consumer demand for fresh and "fresh like" food products increases, the demand for nonthermal methods of food processing is likewise on the rise. In addition, public awareness regarding the dangers of food poisoning is also raising demand for improved food processing methods. Ultraviolet radiation is used in several food processes to remove unwanted microorganisms.

In general the device to be sterilized can be part of any article, instrument, appliance, equipment or any machine.

The present invention can be used in the food industry, were development of microorganisms and/or biofilm can occur e.g. in different segments of dairy processing or in pasteurization lines, wherein devices with lumens are involved in the processing of a (food) product.

Similarly, devices, instruments or components employed in the electronic industry which has lumens, and require being sterile could be target for disinfection/sterilization by the present invention.

The present sterilizing light source can be combined with any other way of disinfection/sterilizing known in the art e.g. gas/vapor/heat sterilization, sonication, use of sterilizing solvents and disinfectants, chemical sterilizing agents, autoclave treatment or using ultrasonic waves.

The "Experiments" section of PCT application no. PCT/EP2009/061286 is hereby incorporated by reference, including the tables 1 and 2, FIGS. 7 and 8, and the related description and discussions section illustrating the disinfecting/sterilizing efficiency of a UV light emitting light source. In relation to a later nationalizing of the present application in the USA the document PCT/EP2009/061286 is incorporated completely by reference.

Further Aspects of the Present Invention

In the present invention the terms "join", "connect", "attach" and "couple" denote a physical connection between two elements through any releasable gripping and/or fastening mean(s) e.g. a locking mechanism, and not merely bringing two elements/structural parts together.

The present invention discloses an assembly, comprising a light source, a separate unit, and a device with a lumen to be disinfected/sterilized. The light source comprises a housing, optionally with an optical lens, and the separate unit comprises an optical window, were the separate unit is placed between the light source and the device, and the separate unit is connected to the light source, at one side of the separate unit, and the separate unit is connected to the device at the other side of the separate unit, whereby the light source gets connected outside, and in extension of the device to be disinfected/sterilized. The material of the separate unit is non-transparent in the sense, that the light emitted from the light source is not transmitted through the separate unit and out into open air. The optical window could also be an integrated or permanent part of the light source.

The presence of the separate unit between the light source and the device enables, one configured light source, to be coupled and adapted to fit different devices/catheters to be disinfected/sterilized. One light source can therefore, in principal, be made to fit all catheters, and it is not necessary to handhold the light source/sterilizing or disinfecting apparatus or the (medical) device to be disinfected/sterilized.

Furthermore, the light source in the present invention does not comprise any moveable mechanical parts/wires, and therefore less maintenance is required. The light source of the present invention functions independently of the device to be disinfected/sterilized, i.e. the light source does not need to be connected to the device to function. This enables that the light source can be tested (before use), without requiring that it is coupled to a device.

Several light sources emitting light with the same and/or different wavelengths having germicidal effects could be coupled together in a unit, wherein optics could capture and guide the emitted lights into the lumen of a device having disinfecting/sterilizing effect. Moreover, a light source could comprise several diodes emitting light with the same and/or different wavelengths having germicidal effects. By this a stronger disinfecting/sterilizing effect could be achieved.

The primary function of conventional catheter hubs is to allow access of liquids such as nutrition, blood, drugs etc. to veins and arteries via the catheter lumen. The hubs or connector parts are not designed for optimal launching of light into a lumen of the device. The Luer connector is the standard used for adapting medical devices and join external equipment such as medical machinery and syringes to indwelling implants such as catheters. The Luer connector system consists of a male and female set that provides a leak proof and mechanically secure connection. The Luer connector system is characterized with ~6% conical male end that fits into a conical shaped female part. Because the Luer connector is the standard coupling system used within the medical field the connector system used for the present invention described has to be designed both to satisfy the demands described in the standards and at the same time allow optimal launch of the light. Normally, Luer connectors end up in a small aperture at the distal end which reduces the germicidal effect of the UV light launched into the catheter tube. This reduction of the germicidal effect is caused by:

1. An aperture/opening in the Luer that is smaller than the inner diameter of the tube. This reduces the amount of light emitted from the diode to reach the interior of the tube which results in reduced disinfection efficiency (area ratio between exit hole in Luer and inner tube diameter is less than 1).
2. A small aperture/opening results in a confined ray of light launched into the tube, which do not reach the inner surface of the frontal end of the catheter tube. This also results in reduced disinfection efficiency.

Moreover, the present invention relates to a coupling device which acts as an interface between the light source and catheter hub. This solves two main issues related to catheter use. The first issue deals with the hygiene between UVC treatments. If the light source should be used repeatedly on the same catheter (i.e. same patient) it has to be disinfected/sterilized before use. If the light source is coupled directly on the catheter hub disinfecting the thread for instance with ethanol would be necessary. This is difficult to do effectively and the light source could actually be a source of contamination. Secondly, all optical surfaces used for diagnostics and treatment have to maintained by cleaning.

If the light source comprises the optical window, this optical window will be in contact with the catheter hub and the saline solutions in the catheter lumen. It is well-known that precipitation of salt and other compounds on optical windows reduces the transmittance of light which results in reduction of the delivered UVC doses in an uncontrollable manner (not possible to administer a specified UVC dose). Therefore it is important that the optical window separating the LED diode can be cleaned and maintained routinely. The suggested coupling portion solves both problems addressed above. It is meant as a disposable unit that can replaced between UVC treatments. Removal of the coupling portion exposes the optical window which can cleaned (with ethanol for instance) if necessary.

These and other aspects, embodiments and advantages of the present invention will become immediately apparent to those of ordinary skill in the art upon reading the disclosure to follow.

DRAWINGS

Embodiments of the invention will now be described with reference to the figures in which:

FIGS. 1a and 1b each show an embodiment of a light source adapted to be part of the assembly.

Figure 4A:
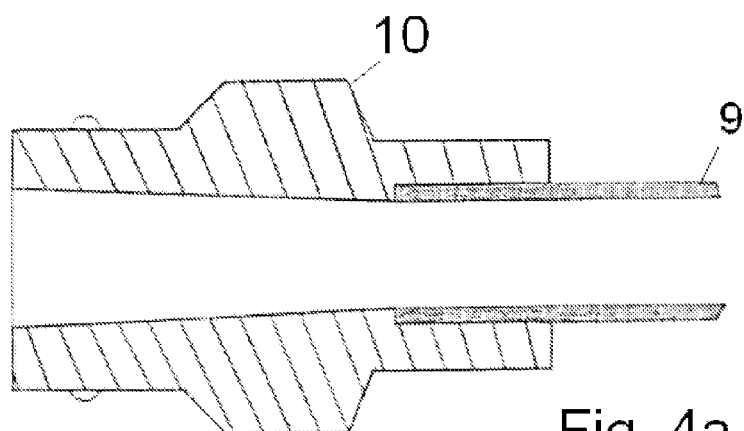
Figure 4B:
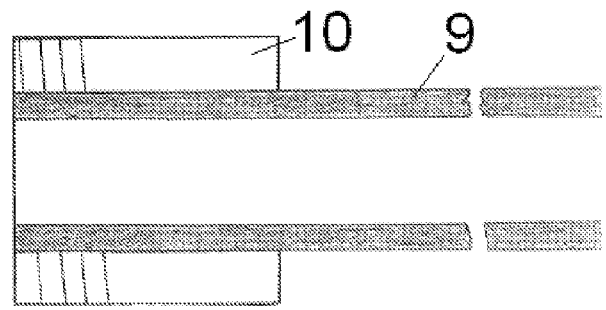

FIG. 4a shows a female Luer connector part that can be mounted on the device. FIG. 4b shows a hub with a cylinder opening. Both hubs allow access of both fluid and light (no obstacles).

Figure 5:
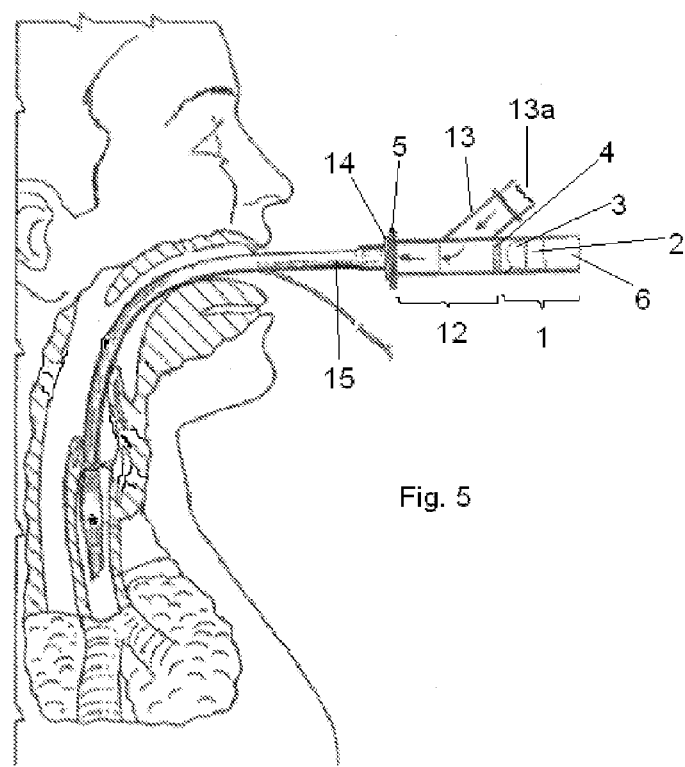

FIG. 5 shows an assembly according to the invention comprising a breathing tube connected with an interface, and a light source in a subject.

Figure 6:
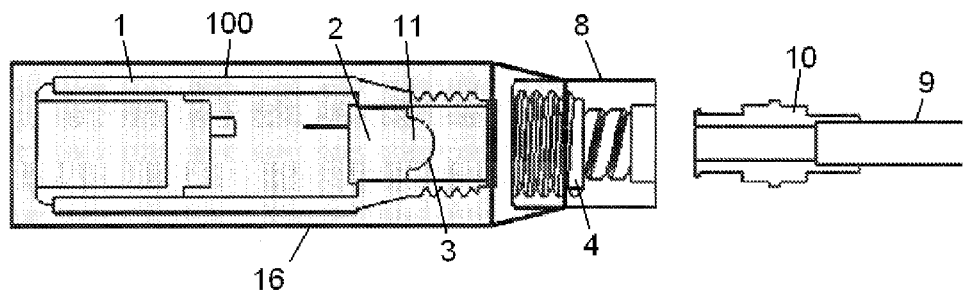

FIG. 6 shows an embodiment of a light source covered with a protective cap.

Figure 7:
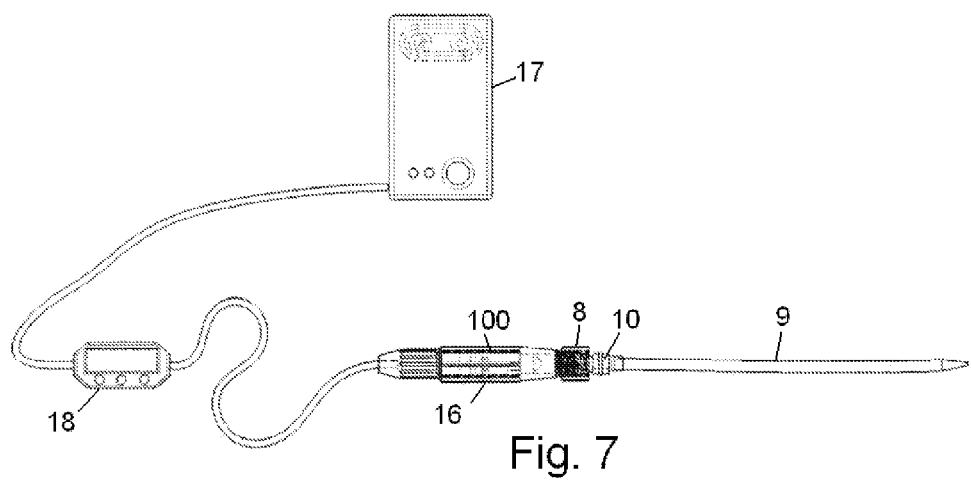

FIG. 7 shows an embodiment of a system comprising an assembly according to the invention together with a power unit and a remote control unit.

Figure 8A:
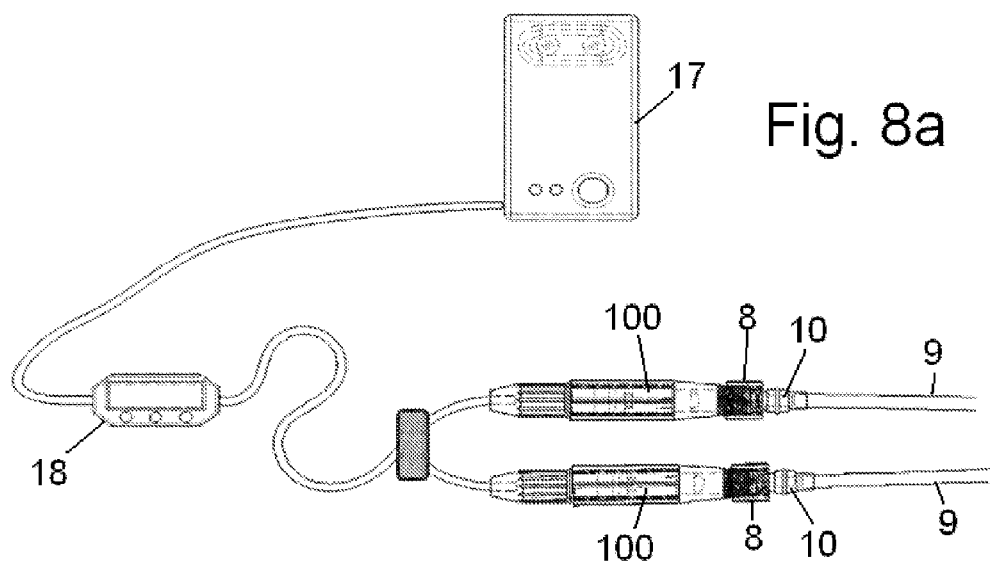
Figure 8B:
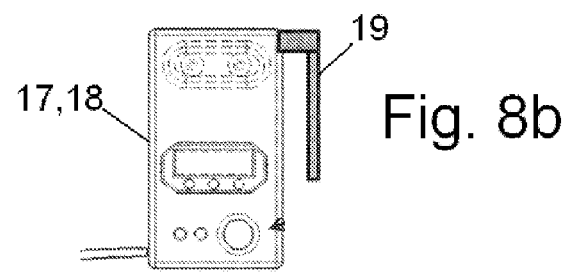

FIGS. 8a and 8b show a other embodiments of systems comprising an assembly according to the invention.

Figure 9:
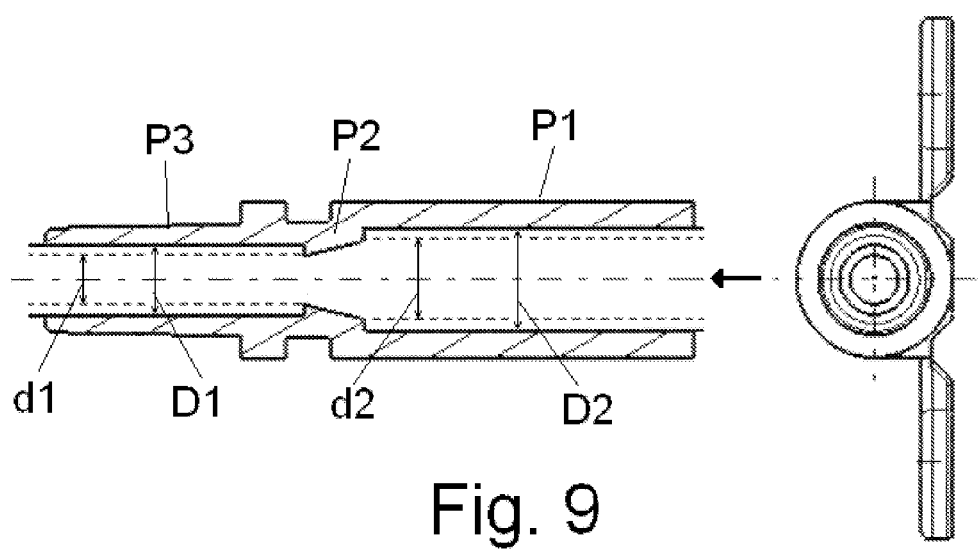

FIG. 9 shows a separate unit being able to connect two tubes which two tubes when connected form a single lumen.

Figure 1A:
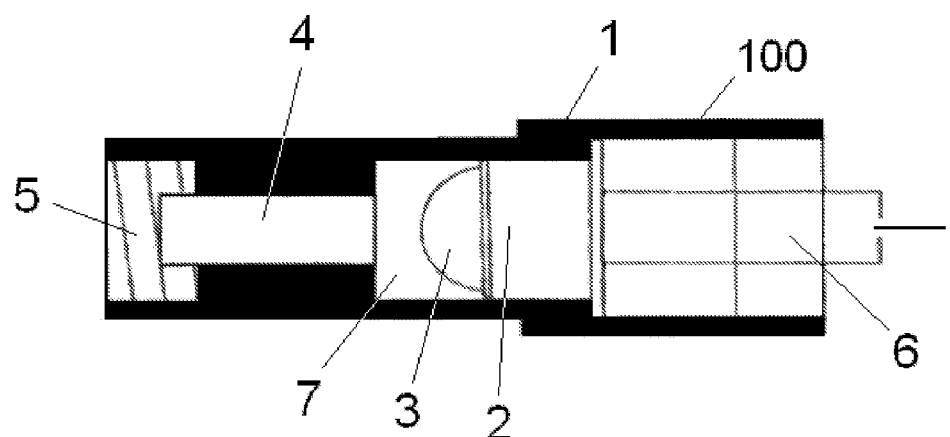
Figure 1B:
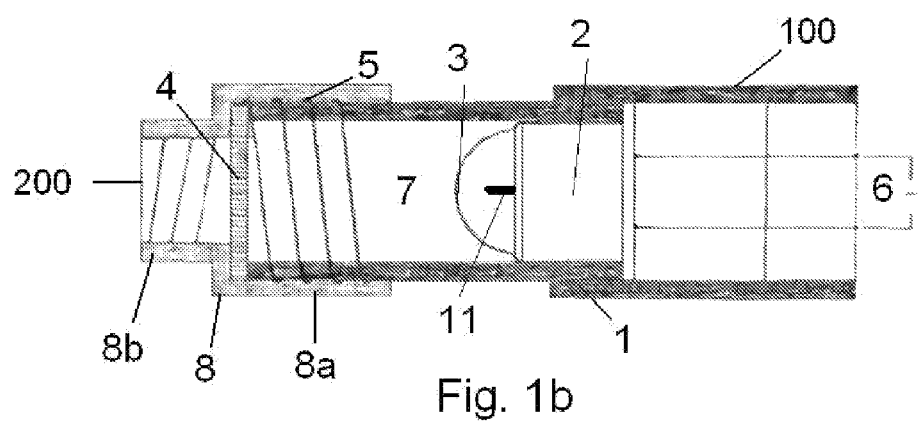

FIGS. 1a and 1b show embodiments of light sources which can be used with an assembly according to the invention. The light source 100 shown in FIG. 1a comprises a housing 1, a a light emitting unit 11 having a socket 2 provided with a source of disinfecting/sterilizing light such as an UVC LED (Light Emitting Diode), an optical lens 3 being e.g. flat, rounded or hemispherical, directing the emitted light from the light emitting unit 11 to an optical window 4 which both focuses and guides and/or at least allows passage of the light to a not shown device inlet and protects the light source 100 from contaminated fluid, a second connector part 5 comprising an inward thread i.e. female part which connector part 5 is connected either directly to a device or to a coupling unit, which during use is secured to the device, and an electrical switch part 6 connected to an electrical power supply. The optical lens 3 can be placed in any distance from the light emitting unit. The light source can also be without the optical lens 3 in front of the light emitting unit 11. The light source can also comprise an optical lens integrated into the light emitting unit 11.

The housing 1 provides a watertight encapsulation for the internal parts. The housing 1 has relatively small dimensions i.e. a length less than 10 cm, usually less than 5 cm, and a diameter less than 2 cm, usually less than 1.5 cm. The housing 1 is usually made of a hard polymer or plastic material (for instance acrylic plastic) or thin metal (for instance alumina), which makes it light, strong and easy to form and manufacture. The housing 1 is at the distal end i.e. the end facing the device equipped with a second connector part 5 making it possible either to link the light source 100 directly to the device via a standard opening in the device, or to link the light source 100 to an interface (not shown) also called a coupling unit (separate unit), which interface enables a link between the specific device and the light source 100. According to the shown embodiment, the second connector part 5 is formed as a female thread fitting into a corresponding male thread on a device for instance Luer conical fitting system or an interface. Thus, in the embodiment in FIG. 1a the optical window 4 is located within the light source, and the light source 100 can be directly coupled to the device, without the need of any coupling part.

The light source shown with this embodiment comprises a light emitting unit 11, e.g. diode equipped with a socket 2 and a ball or hemispherical lens 3. The UV source normally emits light in the range between 200 and 300 nm, which has a disinfecting/sterilizing effect. The space 7 between the optical lens 3 and the optical window 4 is occupied by air through which the UV light passes on the way to the optical window 4. The transparent optical window 4 allows the UV light to pass into the lumen of the device (inner diameters of the tubes are typically in the range 1-5 mm), which is linked to the light source 100, and additionally the optical window 4 provides a watertight barrier which prevents liquid from the device (typically a high refractive index liquid filled into a catheter lumen) to enter the internal parts of the light source 100, or eventually leak to the surroundings. When applying the shown light source it is e.g. not necessary to use optical fibres as the light source 100 can be fastened directly to the device.

During the disinfection/sterilization procedure any liquid inside the lumen of the device is in close contact with the surfaces of the housing 1 and the surfaces of the optical window 4. Therefore it is necessary to be able to clean these surfaces in order to remove residues that otherwise attenuates the UVC light, thereby reducing the efficiency of the light source 100 as the light source 100 normally is used several times. The light source might be used several times with one device and/or it might be used with several devices. The cleaning can be performed with liquid soap, alcohol such as isopropanol or ethanol or another solvent.

In order to be able to guarantee sufficient reduction in the number of germs e.g. bacteria at the inlet portion of the device, it is necessary that internal and/or external structure(s) of the connector part of the device, and/or the device, and/or internal and/or external surface(s) of the light source 100, with or without coupling designs, facilitate the emitted light to reach the inlet portion of the lumen of the device, thereby providing a maximum disinfecting/sterilizing effect. In order to optimize the light entrance into the inlet portion of the lumen of the device, it is advantageous that no part of the light source or of the connector part/hub of the device casts shadows i.e. provide a shade, into the lumen which is to be subjected to the light emitted from the light source. For instance, where a soft medical device tubes is joined to a hub/connector part made in harder polymer protruding edges with a thickness of 1 mm are common. Bacteria will in the shade of these edges multiply rapidly if nutrients are present in the medical device lumen.

Optimal light transmittance conditions will be obtained, if the lumen reaching from the optical window 4 to the lumen "end" has a constant inner or decreasing inner cross sectional dimension and also does not have any protruding parts or edges providing a shade preventing the light from reaching all surfaces. The "end" of the lumen is normally either defined as the working distance of the light from the light source whether the working distance is defined by the intensity of the light or the construction of the device i.e. a bending of the inner lumen of the device.

The inlet portion of the lumen of the device and/or the coupling designs can be coated in any way facilitating the emitted light to reach as much as possible of the lumen of the device providing a disinfecting/sterilizing effect. The coating can be Teflon, a metal layer, e.g. aluminum layer.

The light source is electrically powered, typically 5-10 V, through a connection with the electrical switch part 6, which can be connected to a power supply with electrical cords. The power supply can either be placed at a distance, or it can comprise batteries placed in connection with i.e. joined directly to the light source 100 for flexibility in the clinical setting or at home of the patient. The relative low voltage and current (max 200 mA) allow batteries (rechargeable or not) to be used. This allows cordless light treatment of patient catheters as well as remote treatment far from fixed power installation.

In addition, the light source can be miniaturized with even smaller diodes and electronics, making it possible to place the light source under a sterile bandage placed upon, for instance, a central venous catheter used for hemodialysis. In this application the disinfection/sterilization of the catheter tubes are carried while the patient is at home, and no time is used at the clinic. Next time the patient arrives for another dialysis treatment, the light source is recharged and placed both as a disinfectant/sterilizer and timer (see below) under the new sterile bandage.

The light source can be provided with built-in timer function that can be preset at specific amount of minutes in order to deliver a necessary UVC dose depending of the application. The number of pre-set minutes depends on the electrical current (UVC output), the type of material of the device, e.g. a catheter, the kind of treatment required i.e. the level of catheter contamination being either prophylactic treatments in order to avoid biofilm formation (short treatment times), or longer times if biofilm is formed. A timer function can be part of a UVC light source and represented by a display showing the number of minutes and/or an alarm that beeps, when the exposure time has run out. A computer chip can also be built into the light source, and be programmed to deliver a specified out put in a specific time period.

Maintenance is an important issue ensuring that the correct and expected light output is delivered to the device to be disinfected/sterilized. A separate detector measuring the emitted light and thereby assuring proper performance of the light source can be employed with the present light source before use.

FIG. 1b shows an embodiment comprising a light source 100 having the same or corresponding components as the embodiment of FIG. 1a. Components with same or similar function are provided with the same reference number for the different embodiments disclosed in the present application.

Like the light source 100 shown in FIG. 1a, the embodiment of FIG. 1b comprises a housing 1, a light emitting unit 11 having a socket 2, an optical lens 3 e.g. flat, rounded or hemispherical, an optical window 4 guiding the light to the device inlet, a second connector part 5 which in a state of use connect the light source to a device, and an electrical switch part 6 connected to an electrical power supply. The light source can also be without the optical lens 3 in front of the light emitting unit 11.

The embodiment of FIG. 1b is further provided with a separate unit 8 functioning as an interface having both a female part 8a with an inward thread, which can be connected to the light source 100 and a female part 8b with an inward thread, having a smaller diameter, and which can be connected to a device. This embodiment of the light source assembly and corresponding embodiments provided with an interface placed in fluid tight connection with the optical window 4 is much easier to clean after use.

When a light source including a disposable interface or coupling device or separate unit is separated from the device after use, the disposable interface is removed and disposed of, where after the person handling the device can clean the smooth surface of the optical window together with all other outer surfaces which have been in contact with the patient with disinfecting/sterilizing fluids, if the outer surfaces of the light source are not somehow protected and isolated during use.

When only a single smooth surface is to be cleaned then a cleaning method which only comprises sweeping the surfaces with disinfecting/sterilizing fluid(s) such as ethanol can be considered adequate instead of e.g. subjecting the device to increased heat and/or steam.

In FIG. 1b the cross sectional area of the opening 200 is less than the cross sectional area of the optical window 4 of the light source 100 i.e. it is possible to illuminate the end parts of the device.

When the optical window 4 is provided with proper sealing it can be placed between the interface and the light source 100 simply by turning the two units toward each other. This will make it easy to separate the units, and clean them individually. If the separate unit 8 is to be used more than once, the simple structure of the unit will normally allow for it to e.g. be autoclaved if a proper material has been chosen. The optical window 4 can e.g. be made of UV grade quartz or $CaF_2$ and will normally be 1-2 mm thick.

In another embodiment the cross sectional area of the optical window 4 and the opening of the light source 200 are the same. The light source 100 is provided with a second connector part 5, providing the same inner cross sectional area of the opening of the light source 200 as the optical window 4, facilitating the light emitted from the light source 100 reaching the inlet portion of the lumen of the device providing disinfecting/sterilizing effect of all surfaces at the lumen inlet.

The optical window 4 can have any suitable thickness and be placed at any distance from the optical lens 3 facilitating the emitted light to reach the inlet portion of the lumen of the device, and thereby provide a maximum disinfecting/sterilizing effect. The optimum distance between LED diode or lens system and the tube opening, i.e. the distance where a maximum amount of light is transmitted is normally 3-10 mm for the presently known light sources. But any distance providing an optimal transmission of the light is within the scope of this invention. Similarly, the optical window 4 can have a smaller or bigger cross sectional diameter than the optical lens and/or the opening of the light source 200 facilitating the emitted light to reach the inlet portion of the lumen of the device providing a disinfecting/sterilizing effect.

If a biofilm is established in a catheter and an infection has been diagnosed to relate to the bacterial biofilm in the catheter, removal of the catheter is often the preferred solution. According to PCT application no. PCT/EP2009/061286, which is incorporated herein by reference, it has been demonstrated that it is possible to kill established biofilm in polymer tubes. In order to improve disinfection efficiency with the light source of the present invention, the light source can be equipped with a variable electrical current source.

The total fluence (dose) delivered to the biofilm is a product of the fluence rate and exposure time. In order to reduce the exposure time the fluence rate can be increased in those situations, were a biofilm is diagnosed to be present in the catheter, by increasing the electrical current delivered to the LED diode. The power output of the diode is proportional to the electrical current driving the diodes. The electrical current will be in the range of 20-200 mA. With LED diodes with an output of 2 mW, an exposure time below 10 min is expected, if the light source is used prophylactically. If a biofilm is established, treatment times between 20-60 min can be expected. In order to ensure a long lifetime of the diodes, it is desirable to run them at low currents. This will often be the case when the light source is used prophylactically. In the case with established biofilm, it is desirable to increase the current in order to reduce the UVC exposure time to a minimum. Accordingly, a unit powering the UVC light source which is designed to deliver a variable amount of current can also be employed, depending on the circumstances.

Another problem with established catheter biofilm is that the bacterial cells are close in space in the extracellular matrix of the biofilm. The UVC light is therefore scattered and absorbed strongly through its way in the biofilm. This is the main reason why the germicidal efficiency of the UVC light is much lower in the biofilm, than in water. The bacterial cells can be shadowed by others and as such better protected against the UVC exposure. If the direction of the UVC photons illuminating the biofilm can be varied dynamically, more cells can be exposed and killed and thereby increasing the disinfecting/sterilizing efficiency.

Preliminary data indicate that no reduced transmittance occurs by moving the light emitting unit and lens or lens a few mm on both sides of the focal point. The distributions of the photons transmitted by internal reflections inside the tube take will, however, be totally different and as result more cells will be exposed. It is therefore desirable, that the optical lens can be moved forward (towards the inlet portion of the lumen of the device to be disinfected/sterilized) and backwards, e.g. manually, mechanically/electrically by pushing a button on the light source.

Moreover, it is important to keep a sterile barrier between the UVC light source and catheter. In the invention shown in FIG. 1b, the liquid from the catheter lumen is in direct contact with the optical window 4 (UVC transparent window). During UVC exposure, this window will be disinfected by the high fluence delivered to this part of the assembly. In another embodiment the optical window 4, can be placed in the separate unit 8, as illustrated in FIG. 2 and FIG. 2a (enlargement of the coupling part in FIG. 2).

Figure 2:
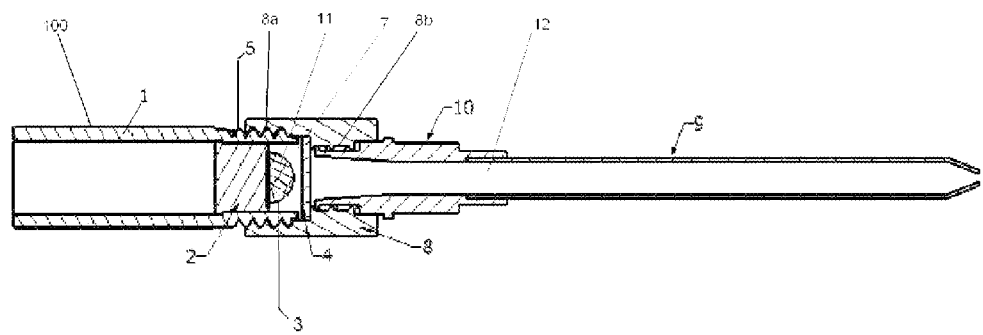
FIG. 2 shows an assembly according to the invention comprising a device in form of a catheter and a light source, were the optical window is an integrated part of the separate unit.
Figure 2A:
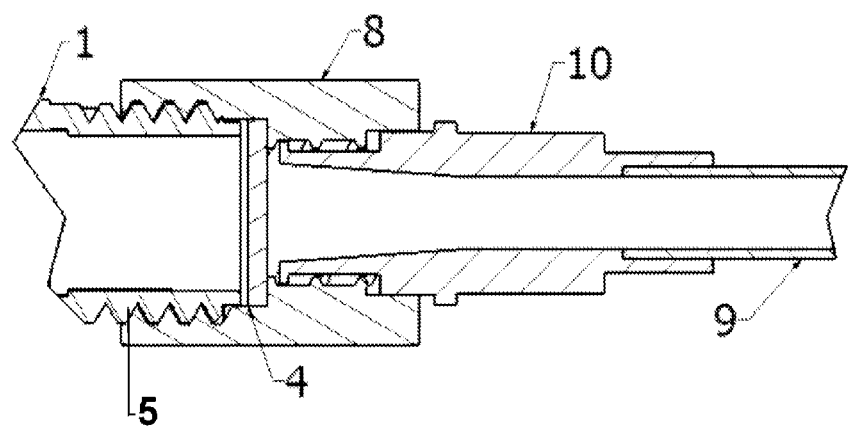
FIG. 2a shows an enlargement of the coupling between the device and the light source of FIG. 2.

FIG. 2 shows an assembly according to the invention. The assembly comprises a light source 100 with a second connector part 5, a separate unit 8 comprising an optical window 4, a connecting female part 8a having an inward thread and adapted to connect to the light source 100 and a connecting female part 8b having an inward thread and adapted to connect to a device, a device in the form of a catheter 9 having an inlet hub i.e. a first connector part 10 and an open inner lumen reaching from the optical window 4 of the light source to the lumen end, which generally is defined as the distance where the light no longer works effectively e.g. the distal end of a catheter, which open lumen has a constant cross sectional area. The light source further comprises a light emitting unit 11, which is placed in front of the optical lens 3. But the light source can also be without the optical lens 3 in front of the light emitting unit 11. The light source can also comprise an optical lens integrated into the light emitting unit 11.

Firstly, the separate unit 8 with the optical window is assembled with the light source 100. The light source 100 is fastened to the separate unit 8 by (a) fastening or connecting mean(s) e.g. by screwing, providing a watertight contact between the separate unit 8 and the light source 100. A gasket can also be placed between the separate unit 8 and light source 100, ensuring a water tight connection. The window can also be joined to the separate unit 8 in such a way that no gasket is needed.

After the light source 100 has been assembled with the device, e.g. a catheter, the light treatment e.g. with UV-C light can be initiated. Before joining the assembly, the catheter can be filled with a light guiding liquid (12), e.g. an aqueous solution of for instance sodium chloride for optimal guidance of the light through the first connector part 10 and tube/catheter lumen.

Liquid light guiding is based on the phenomena that if the liquid core has a higher refractive index than the tube wall, internal reflections of light launched into a tube opening are forced to propagate along the inner lumen of the tube. The situation is complex in the LED diode—catheter tube case because the light emitted from the diode, and focused by the lens is emitted in an angle of several degrees into a tube having a rough surface due to the manufacturing process. Therefore light rays impinging on the surface the first time are much likely reflected into different angles, and are impinging next in other angles. In theory, the critical angle, $\theta_c$ above which all light rays are internally reflected is expressed by the ratio of the two refractive indices: $n_w$ (wall) and $n_l$ (liquid) as:

$$\Theta_c = \sin^{-1}(n_w/n_l)$$

If the refractive index of the liquid is increased, for instance by adding more NaCl, more light is transmitted through the tube. This is convenient in the catheter case as it is desirable that as much light as possible is transmitted to the distal end of the catheter in order to 1) make as many light photon reflections internally in the catheter tube lumen as possible, such that the inner surface is effectively exposed and 2) to be able to disinfect the distal end of the catheter. The loss of light, which is measured as a reduced transmittance (even in clean tubes) is caused by absorption in the thick tube walls and in biofilm constituents such as bacterial cells, when these are present in the catheter lumen. Those light rays striking the surface in an angle below the critical angle, penetrates a few fractions of a millimeter before they are totally absorbed. Only a few percent of UVC light penetrates a wall with a 1 mm thickness even if the material is semi-transparent in the UVC spectral region.

In some devices it can also be advantageous to be able to disinfect/sterilize the outer surface and the inlet portion of the device, which is touched and handled by e.g. nurses. Especially in those situations, were it is critical that no germs e.g. bacteria are present, and/or the device is placed for only a short time. Catheters made of such transparent or semitransparent materials can be used according to the method suggested for disinfection of the outer surface of lumen of the device. It is necessary in this case to use tubes made of transparent materials with a thin wall. Such materials are for example various Teflon and Plexiglas types.

Light guiding liquid(s) or solution(s) which can also be termed light propagating or transporting or light transparent medium are liquid(s) that increase the transmittance of the emitted light from the light emitting unit and such liquid can be filled into the lumen of the device lumen. The light guiding fluids could be any non-hazardous and pharmaceutically acceptable/safe solution(s) and/or fluid(s), having a refractive index higher than the refractive index of the material constituting the inner surfaces of the device. The skilled man would know, in which amounts specific solutions and fluids should be employed to be non-hazardous and pharmaceutically acceptable for use in the present invention. Examples of light guiding non-hazardous, cheap fluids which are easily available in the clinic are e.g. based on sodium chloride, NaCl in concentrations from 0.9% to 30%. Saline solution can be made to span the refractive index interval between 1.34-1.37 if increasing amounts of NaCl are dissolved in water. Other non-hazardous compound can be used but these will be more expensive and absorptive than common used sodium chloride.

The separate unit 8 can also be connected to the device e.g. a catheter when the device is not in use, as it can e.g. be working as a closure cap sealing of the catheter opening. When disinfection/sterilization of the catheter is required, the light source can be connected to the separate unit.

FIG. 2a shows an enlargement of the separate unit 8 with the optical window 4, used in FIG. 2. After the separate unit 8 has been fastened to the light source 100, the separate unit 8 is then fastened to the device by screwing it on the catheter inlet hub 10, which is also referred to as the first connector part 10. The space 7 between the optical lens 3 and the optical window is occupied by air or by a transparent fluid through which the light emitted from the light emitting unit 11 passes on its way to the optical window 4. There is no overlap of the structure of the device and the housing 1 of the light source 100 when the assembly is in use, this means that the two units are positioned in extension of each other and the total length of the assembly is at least the length of the housing of the light source plus the thickness of the optical window plus the length of the device. The inlet portion of the device to be sterilized/disinfected and the opening part of the light source 100 is embedded and/or fixed within the separate unit 8 when the assembly is in use.

FIGS. 2 and 2a show a separate unit 8 acting as a sterile barrier between the light source 100 and the device first connector part 10. The sterile barrier is provided by optical window 4, between the two opposite coupling portions of the separate unit 8. The optical window 4 can be made of inorganic transparent materials, such as UV grade quartz or $CaF_2$. More conveniently the window is made of light transparent, normally UVC transparent polymers, for instance various types of Teflon, plexi glasses etc. Instead of an optical window, any mechanical stable watertight light transmittant barrier e.g. in the form of a film or a sheet can be used, which can transmit the light into the lumen of the device to be disinfected/sterilized, providing a close watertight barrier.

Figure 3:
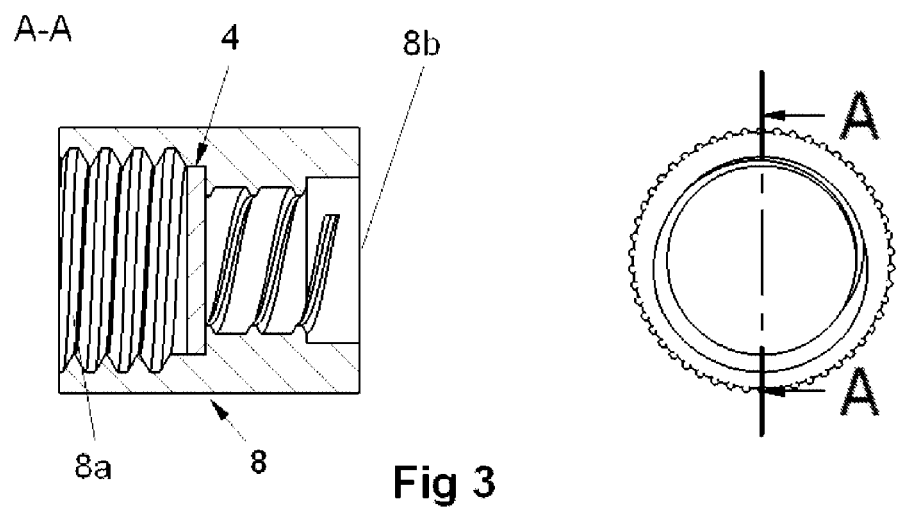
FIG. 3 shows an embodiment of an interface/separate unit suitable to be used with the assembly.

The light source 100 is placed in axial extension of the separate unit 8, being coupled to the first connector part 8b of the separate unit 8 (FIG. 3). The device to be sterilized is placed in axial extension of the separate unit 8, being coupled to the second connector part 8a of the separate unit (FIG. 3).

FIG. 3 shows a separate unit 8 functioning as an interface and having two oppositely placed coupling positions. A first coupling part 8b is to be coupled to a corresponding second connector part 5 of a light source 100, and a second coupling part 8a is to be coupled to a corresponding first connector part 10 of a device.

The first coupling part 8b is located at one side of the optical window 4 of the separate unit and the second coupling part 8a is located on the other side of the optical window 4 of the separate unit. There is no overlap of the first and second coupling part of the separate unit 8, i.e. the first and second coupling part of the separate unit 8 extend in axial opposite directions from the optical window within the separate unit 8. The axial (horizontal) direction is the direction of the pathway of the emitted light from the emitting light unit 11.

The separate unit 8 encloses or encompasses the inlet portion of the device or at least a portion of the inlet portion of the device at one side of the optical window 4 and encloses or encompasses the opening part of the light source 100 or at least a part of the opening part of the light source 100 at the other side of the optical window 4 when disinfection/sterilization takes place. The optical window 4 is configured to provide a complete separation i.e. form a sterile barrier, between the two units i.e. the device and the light source, and prevent contamination of the light source.

The separate unit 8 can also be placed and connected to the light source 100 and the device such that there is no part of the device or the light source 100 which overlaps the optical window 4 of the separate unit 8, i.e. no parts of the device or the light source is/are above or under the optical window of the separate unit 8.

The light source 100 is placed outside, and in extension of the separate unit 8, coupled to the first connector part 8b of the separate unit 8. The device to be sterilized is placed outside, and in extension of the separate unit 8, coupled to the second connector part 8a of the separate unit.

To achieve optimal disinfection conditions the use of a modified male Luer connector end fitting into a standard female end is preferred. This allows optimal access of light into the lumen of the device and satisfies both the need for liquid access and optimal launching of the light into the device. The major advantage of placing the optical window 4 in the separate unit 8 is that a sterile barrier between the light source and device to be disinfected/sterilized is provided. Another advantage compared to the solution depicted in FIG. 1b is, that there is no maintenance of optical surfaces between treatments/use of the device for disinfection/sterilization. In addition, if the window is a UV transparent polymer, it can be joined to the other polymer parts of the separate unit such that it provide a sealing of tube lumen and liquids therein during UVC treatment of the tube lumen i.e. no gasket or o-ring is needed then.

The connector part is typically of Luer type with a 6° conical shape as indicated in FIG. 2 In addition, no shadowing is present between the connector 10 and the (catheter) device 9. The light emitting unit 11 (e.g. UV LED diode) is powered by a low DC voltage source, e.g. 6 V. Typically a few hundreds microwatts up to a few milliwatts of UVC light is emitted from such a diode depending of the applied electrical current. The optimal wavelength used for disinfecting/sterilizing purposes is between 250-280 nm. An optical path length (1-5 mm) between the diode/lens system and edge of the first connector part 10 ensures that light is optimally launched, and that the inner lumen of the inlet is exposed to UVC light to a degree, where disinfection/sterilization takes place.

The optical window 4 can be inserted and fixed or connected to the polymer material of the separate unit 8 by heat treatment and welding. The optical window could also be inserted, fixed e.g. clicked into place in the separate unit manually, and be reused after disinfection/sterilization or changed when appropriate.

The optical window 4 can have any suitable thickness, and be fixed at any place in the separate unit 8, i.e. at any distance from the light emitting unit 11, or optical lens 3, facilitating the emitted light from the light emitting unit to reach the inlet portion of the lumen of the device, and thereby provide a maximum disinfecting/sterilizing effect. The optimum distance between the optical lens 3 and the lumen opening, i.e. the distance where a maximum amount of light is transmitted is 3-10 mm. But any distance providing an optimal transmission of the light is within the scope of this invention. Similarly, the optical window 4 can have a smaller or bigger cross sectional diameter than the optical lens 3, and/or the opening of the light source 200, facilitating the emitted light to reach the inlet portion of the lumen of the device, providing a disinfecting/sterilizing effect. Both the light source and the separate unit can also comprise an optical window, were the optical window in the light source is placed in front of the light emitting unit or the optical lens. An optical window as a part of the light source is easily cleaned, and will help protecting the light emitting unit/element and/or optical lens against impurities, which might result in a decreased dose of emitted light reaching the inlet portion of the device to be disinfected/sterilized.

The major advantage of placing the optical window 4 in the separate unit 8, is that there is a sterile barrier between the light source and device to be disinfected/sterilized. In this embodiment several different separate units can be designed with different optical windows, e.g. optical windows fixed at different positions within the separate unit 8, and/or having different thicknesses and transmittance, that can be employed in different situations depending on the use, i.e. either prophylactically or having disinfecting/sterilizing effect.

If the separate unit 8 is to be used more than once, the simple structure of the unit will normally allow for it to e.g. be autoclaved if a proper material has been chosen. The optical window 4 can be made in relative cheap materials and will normally be disposable.

In yet another embodiment the entire housing of the light source is made in a cheap material making the housing to a disposable unit to be changed between light treatments of different patients. If the lifetime of the diode has not been reached, the disinfection/sterilization unit could then be used for light treatment of a new device while still maintaining a high level of hygiene simply by changing the polymer housing to a sterile one. This will reduce the overall cost of each device treatment. A disposable housing will expose the light emitting unit 11, making it possible to change the light emitting unit 11 manually, for example after it has expired and/or its efficiency is reduced.

The purpose of the present invention is mainly to sterilize/disinfect lumens or surfaces of devices prophylactically, avoiding infections e.g. in the form of bacterial deposition and/or production of bioflim. The intention is to mainly use the invention as a preventative mean i.e. by disinfecting the inner surfaces of the connector part and outermost/inlet portion of the lumen of the device. Therefore preventative light treatments of the entrance of devices with the described invention will normally take place right after the device e.g. a catheter has been inserted into a subject, and thereafter e.g. be repeated before and after use of the device e.g. before and after a haemodialysis session. No contamination of the inner surface of newly inserted catheters is normally expected. If the catheter is contaminated and a biofilm is established intra luminal catheter salvage can be possible using the assembly by administering longer light treatment periods. During handling of the devices i.e. opening and closing of inlet hubs by personnel, contact to the patient's skin and exposure from external possible sources of germs e.g. bacteria, such as equipment e.g. syringes and tubes, bacteria can penetrate through the connector part and start colonizing the inner lumen. Therefore, it is important to disinfect/sterilize as much of the proximal end of the device immediately after it has been handled in order to prevent biofilm formation, which eventually later on could be spread to other parts such as distal ends of a catheter being in contact with the patient. After the light source 100 has been coupled to the inlet portion of the device, e.g. a catheter, which is to be sterilized/disinfected, the light source 100 and the catheter might be aligned avoiding bending of the catheter. Although it is possible to sterilize/disinfect Teflon tubes having a moderate bend, any bend in the catheter which decreases the emitted light from reaching the inlet portion of the device providing disinfecting/sterilizing effect, should be avoided.

Shadowing effects in the device have been demonstrated to reduce the UVC disinfection efficiency. FIGS. 4a and 4b illustrate possible solutions to remove shadowing effects from the Luer connector device. In FIGS. 4 and 4a there is no edge between the Luer and the catheter tube.

FIGS. 4a and 4b show two embodiments of a first connector part 10 attached to a catheter tube 9, where the joined first connector part 10 and catheter tube has the same inner cross sectional area as the lumen of the catheter. This can be obtained either by providing the inner surface of the hub i.e. the first connector part 10 with a cut-out in the inner surface facing the catheter tube which cut-out is deep enough to contain the cylindrical walls of the catheter tube as shown in FIG. 4a or to let the hub i.e. the first connector part 10 surround the catheter tube in such a way that the catheter tube is in level with the outer end-surface of the hub as shown in FIG. 4b. The first connector part 10 is in both embodiments formed with a male thread (illustrated by small bulks on the outer surface at the open end of the catheter in FIG. 4a and with lines in FIG. 4b). This allows both light to be launched effectively into the tube lumen of the catheter 9 and liquids to be flushed through the lumen of the first connector part 10 having a straight cylindrical shape and the same inner diameter as the tube lumen. The first connector part 10 can be glued, welded or molded directly at the outer side of the catheter tube i.e. the outer diameter of the tube fits into the inner diameter of the first connector part. With no edges and no dead locks between the first connector part 10 and the tube lumen no reduction of light will be observed when the light is launched into the lumen. With this design no parts of the first connector part 10 is shaded and able to harbor microorganisms due to deadlocks.

Another solution can be to insert and join the tube in a recess of the first connector part 10. The first connector part 10 can be made of all kinds of polymers or coated polymers, especially of Teflon which has a low refractive index ensuring optimal light propagation. Normally the connector part 10 is molded.

All polymer parts that are employed to join the tube and the Luer connector could be made in UVC transparent polymer, e.g. various Teflon materials. Moreover, catheters are made with multiple lumens. The ex-vivo parts of the multi-lumen catheter are normally separated such that each tube lumen can be accessed in a flexible way i.e. the tubes are separated. In the in-vivo part the tubes are normally joined into one fixed polymer unit, with two lumens. In the situation where they are joined it is equally important that no shadowing effects are present. The junctions between the ex-vivo and in-vivo part of the lumens should fulfill the same requirements as those stated above concerning the Luer—tube interface in order to obtain 100% disinfection in the entire catheter lumen from Luer connector to catheter tip.

FIG. 5 shows another embodiment of an assembly according to the invention which embodiment comprises a Y-piece, with a channel/duct for ventilator air and a channel/duct for UVC light is connected to the ET tube. The Y-piece allows both air from the ventilator to enter the ET tube through one channel simultaneously with UVC light is launched into ET tube via the other channel. The UVC light source is placed at the same axis as the center of the ET tube, in order to reduce the loss of light caused by an off axis position of the UVC light source.

More particular, FIG. 5 shows an ET tube/breathing tube 15 having a first end 14 provided with a connector part and a second end inserted in the trachea of a subject, and a light source having a modified interface 12 provided with a corresponding connector part 5. The modified interface 12 is attached to the breathing tube 15 at the first end 14 in extension of the proximal end of the lumen of a breathing tube 15 which is inserted in a subject. In this case the modified interface 12, and the light source might be an integrated unit, being inseparable but normally the light source and the modified interface 12 is constructed as two independent parts. The modified interface 12 comprises a by pass 13 with a lumen 13a through which air or other gasses passes back and forth, rendering it possible to attach the combined modified interface 12, and light source to the breathing tube 15 permanently. The inner diameter of the lumen of the breathing tube 15 is often bigger than the diameter of catheters, e.g. up to 10 mm and accordingly, the connecter part 5 of the modified interface 12 has a corresponding size and is e.g. unthreaded, threaded, including luer, press fit, and has bayonet type couplings. The combined modified interface 12 and light source when attached to the proximal end of the breathing tube 15 at 14, constitute a relative rigid portion providing disinfection/sterilization of the modified interface 12 through which air or gasses flows, and the proximal lumen of the breathing tube 15. In another embodiment the lumen or a part of the lumen of the breathing tube 15 could be coated with a metal layer, e.g. aluminum, ensuring that the emitted light from the light source is guided to the second end of the breathing tube 15.

The transmission properties of the endotracheal tube with the LED light source shown in FIG. 5 can be optimized, if the polymer tube is coated with aluminum or an aluminum folio is glued or attached to the inner surface by other means. In addition, the variable current and movable LED-lens options can be used here too.

FIG. 6 shows an assembly according to the invention comprising a light source 100, a separate unit 8 and a medical device. A protection cap 16 is at one end attached to the separate unit 8, as the protection cap 16 is made of a soft and flexible material it is possible to position the light source 100 inside the protection cap 16 and afterwards fasten the light source to the separate unit 8. The material will normally be a thin polymer or plastic which effectively will separate the light source from the surroundings and prevent contact between the light source and the patient. The protection cap 16 will therefore prevent contamination of the light source and simplify cleaning of the light source between treatments or make cleaning of the light source unnecessary as the light source will not be in direct contact with any of the patients.

When finishing a treatment the separate unit 8 will first be detached from the medical device which in this case is a catheter and then the separate unit 8 together with the light source will be removed from the patient. Then the separate unit 8 together with the protection cap 16 will be detached from the light source 100 which have been completely covered by the protection cap 16. The separate unit 8 together with the protection cap 16 is a disposable unit which will be thrown away whereas the light source 100 is ready to be used again.

Generally, according to one embodiment of the assembly according to the invention a thin, transparent and completely water tight foil can be placed inside the disposable separate unit 8. This way the foil can eliminate contact between the light source and the solution in the device lumen and it will not be necessary to clean a fixed front window in the light source.

FIG. 7 shows a complete system where an assembly according to the invention is applied. Beside the assembly the system further comprise a power unit or transformer 17 comprising a built-in light detector which is used for maintenance check and an external control unit or timer 18 which are used to control the light transmitted from the light source of the assembly.

When putting the system to work the separate unit 8 is first connected to a light source, normally a UVC light source. This establishes a sterile barrier to the lumen of the medical device which in FIG. 7 is shown as a catheter. Next, the joined separate unit 8 and light source is connected to the catheter hub 10. Then the light treatment of the intra-luminal space of the catheter is initiated. Preset time intervals corresponding to light doses determined for a specific clinical problem (type of catheter, level of bacterial contamination etc.) can be set on the light source or via an external control unit 18. One advantage of using a remote control is that the electronic parts are excluded from the light source. This makes the device lighter and easier to interface to the patient catheter without dragging the ex-vivo tubes and thereby avoid producing a force on the catheter insertion site/wound. A beeper is optional in the remote control in order to advice the staff that the light treatment is ended. Another feature is that when the set light treatment time has been reached the remote control power off the light source automatically. A 1-3 m electrical cord from the remote control to the transformer 17 ensures that the light source can be powered up. Typical power requirements are 5-6 V DC and 20-200 mA. A light detector unit can be built-in the transformer unit 17. This makes it possible to carry out maintenance check of the light source close to the bedside In FIG. 7 it is illustrated how a protection cap 16 can cover the outer surfaces of the light source while being attached to the inside of the opening of the separate unit 8 contrary to the embodiment of FIG. 6 where the protection cap 16 is attached to the outer surfaces of the separate unit 8.

FIGS. 8a and 8b illustrates systems with which an assembly according to the invention can be employed. The system shown in FIG. 8 comprises two light sources which can be combined either with two single lumen catheters or with a single two lumen catheter e.g. a two lumen UVC disinfection device. For instance, CVCs used for hemodialysis is normally a two-lumen catheters. One lumen is used to draw blood and the other is used to return dialyzed blood back to the patient again. Dialysis patients prefer to spend as short time as possible in dialysis and disinfecting both set of hubs and lumens in parallel will reduce the light treatment time. The multi-lumen light disinfection device system shown in FIG. 8a could be applied in this situation, in this system two identical light sources are placed in parallel and controlled from the same remote control.

Generally, it would be possible to construct a system with more than two light sources and place all the light sources in parallel.

FIG. 8b shows a combined power support and control unit e.g. comprising a detector for maintenance check. The unit is normally provided with a rechargeable battery and a handle 19 for mounting the power supply on e.g. a bedside. Between treatments i.e. in periodes where the system is not in use, the UVC system can e.g. be placed in a safe grip in the power supply unit and the rechargeable battery can be loaded. During use the power unit with remote control unit 17, 18 can be placed at the bed by the handle 19 such that no electrical cords have to be drawn between the bed and a power supply socket in the wall.

FIG. 9 shows a separate part connecting 2 tubes forming a single lumen creating no shadows in the entire lengths of the two connected tubes. The disinfecting light e.g. UVC light enters in the direction of the arrow at the proximal opening of a tube P1 with a larger diameter and through a continuous transition P2 part having a decreasing diameter the light enters the tube P3 with a smaller diameter. D1 is the inner diameter of the smallest part of the connector and D2 is the inner diameter of the largest part of the connector, d1 is the inner diameter of a tube positioned in the smallest part of the connector and d2 is the inner diameter of a tube positioned in the largest part of the connector. The same connecting part can be used in multi-lumen tubes/catheters.

At the moment UVC light is normally used for treatments according to the invention but any light showing sterilizing or disinfecting effect on present micro organisms can be used. Other relevant light types can be UVA, UVB or visible light.

The inner lumen surface(s) of a device 9 might be coated or extruded with a material having a low refractive index e.g. a thin layer of teflon material or gels or the like, which material decreases the refractive index, improves the light transmittance and even preserves the soft mechanical properties of the devices. The low refractive index will also guide the light when ions controlling the refractive index of the water are present in the water.

The inner lumen surface(s) of a device 9 might also be provided with a photo active coating such as $TiO_2$. A coating with $TiO_2$ will when illuminated with a UV light at a wavelength of 375 or lower will cause the coated surface to be cleaned.

If the lumen walls of the device 9 are made of a material transparent of light such as UVA or UVB light or a material which is partially transparent e.g. a polymer, it would also be possible to disinfect the outer surfaces of the lumen of the device 9.

The invention claimed is:

1. An assembly comprising:
   a device for transporting fluid having a lumen and a connector part,
   at least one light source configured to emit light having disinfecting/sterilizing effect, and
   a separate unit;
   wherein the light source comprises:
   a housing comprising a light emitting unit emitting light having disinfecting/sterilizing effect and a connector part;
   and where the separate unit comprises:
   an optical window being transparent for light emitted from the light emitting unit,
   a first coupling part and a second coupling part comprising respective releasable gripping and/or fastening mean(s), where the first coupling part during use is attached to the connector part of the light source, and the second coupling part during use is attached to the connector part of the device, such that the device is in complete extension of the light source with no overlap meaning that the light source will emit light on the end parts of the device while the device will not touch the light source due to the optical window separating the device from the light source, and the first coupling part is located at one side of the optical window with no overlap of the first and second coupling part of the separate unit, when disinfection/sterilization of the device takes place.

2. An assembly according to claim 1, wherein the connector part is formed in such a way, that no protruding parts create shadows in the connector part and its lumen.

3. An assembly according to claim 1, wherein the connector part is a standard female Luer connector part with no protruding or UV non-transparent parts producing shadows in the lumen of the device.

4. An assembly according to claim 1, wherein the light source comprises a housing which comprises a light emitting unit, which emits light having disinfecting/sterilizing effect or a photoactive effect, and an optical lens, which focuses the emitted disinfecting/sterilizing or photoactive light, and a second connector part.

5. An assembly according to claim 1, wherein the light source emits light having a wavelength between 250 nm and 700 nm.

6. An assembly according to claim 1, wherein the light source further comprises an indicator adapted to show the expected life expectancy of the light emitting unit, being able to deliver a light having disinfecting/sterilizing effect.

7. An assembly according to claim 1 wherein the light emitting unit emits UVA or UVB or UVC or visible (VIS) light.

8. An assembly according to claim 7, wherein the light emitting unit is a UVA, a UVB, a UVC or a VIS LED diode.

9. An assembly according to claim 1, wherein the device comprises a separate connector part combining to separate tubes which separate connector part has a continuous transition having a constant or decreasing inner cross-sectional area.

10. An assembly according to claim 1, wherein the assembly comprises more than one light source to be combined with one or more devices via a separate unit.

11. An assembly according to claim 1, wherein a light source is combined with a protective cap which together with the separate unit completely covers the light source.

12. An assembly according to claim 11, which protective cap is made of a flexible material.

13. An assembly according to claim 1, wherein the assembly comprises a power unit, e.g. comprising batteries and a remote control used to control time intervals for light doses.

14. An assembly according to claim 13, wherein the power unit is provided with a handle used for mounting the power unit close to the patient without the patient actually carrying the power unit.

15. A method for disinfecting/sterilizing a device of an assembly according to claim 1, the method comprising the steps of:

a) coupling the separate unit to a first part being either a device or a light source;
 b) coupling the separate unit to a second part being either a light source or a device;
 c) switching on the light source, and disinfecting/sterilizing the device for a defined time period;
 d) disconnecting the light source from the separate unit.

16. A method according to claim 15 which further comprises the step of:
 filling the lumen of a device to be disinfected/sterilized with a light guiding fluid, before coupling the separate unit to the device.

17. A method according to any of the claim 15, wherein the material of the lumen of the device to be disinfected/sterilized, and/or the light guiding liquid(s) within the said lumen are chosen such that disinfection/sterilization of the outer surface of the lumen of the device is obtained.

* * * * *